United States Patent [19]

Outtrup et al.

[11] Patent Number: 5,597,720

[45] Date of Patent: Jan. 28, 1997

[54] ALKALINE PROTEASE FROM BACILLUS SP. PD498, METHOD OF MAKING AND METHOD OF USE

[75] Inventors: Helle Outtrup, Ballerup; Claus Dambmann, Søborg; Dorrit A. Aaslyng, Roskilde, all of Denmark

[73] Assignee: Novo Nordisk A/S, Bagsvaerd, Denmark

[21] Appl. No.: 325,386

[22] PCT Filed: May 26, 1993

[86] PCT No.: PCT/DK93/00183

§ 371 Date: Oct. 26, 1994

§ 102(e) Date: Oct. 26, 1994

[87] PCT Pub. No.: WO93/24623

PCT Pub. Date: Dec. 9, 1993

[30] Foreign Application Priority Data

May 27, 1992 [DK] Denmark ................... 0702/92

[51] Int. Cl.⁶ .................. C12N 9/50; C12N 9/52; C12N 9/54; C12N 9/56; D06M 16/00
[52] U.S. Cl. ................ 435/221; 435/219; 435/220; 435/222; 435/264; 510/530
[58] Field of Search ................. 435/219, 222, 435/264; 252/174.12, DIG. 12

[56] References Cited

U.S. PATENT DOCUMENTS

| | | | |
|---|---|---|---|
| 4,052,262 | 10/1977 | Horikoshi et al. | 435/221 |
| 4,480,037 | 10/1984 | Ichishima et al. | 435/221 |
| 4,764,470 | 8/1988 | Durham et al. | 435/221 |
| 4,771,003 | 9/1988 | Stellwag et al. | 435/221 |
| 5,362,414 | 11/1994 | Outtrup et al. | 252/174.12 |

FOREIGN PATENT DOCUMENTS

| | | |
|---|---|---|
| 3328619 | 2/1985 | Germany . |
| 45-009230 | 4/1970 | Japan . |
| 1-101884 | 4/1989 | Japan . |
| 2-195878 | 8/1990 | Japan . |
| 6-261751 | 9/1994 | Japan . |
| WO92/17577 | 10/1992 | WIPO . |
| WO92/17576 | 10/1992 | WIPO . |
| WO92/17578 | 10/1992 | WIPO . |

*Primary Examiner*—David M. Naff
*Assistant Examiner*—Jon P. Weber
*Attorney, Agent, or Firm*—Steve T. Zelson, Esq.; Cheryl H. Agris, Esq.

[57] ABSTRACT

An alkaline protease has been isolated from Bacillus sp. PD 498 which has a mass of 34 kD by SDS-PAGE, a pH optimum of 9–11, a pI of 9.3, and a temperature optimum of 40°–55° C. The protease has been formulated into detergent additives and detergents and is suitable for washing processes.

14 Claims, 3 Drawing Sheets

ALKALINE PROTEASE FROM BACILLUS SP. PD498, METHOD OF MAKING AND METHOD OF USE

CROSS-REFERENCE TO RELATION APPLICATIONS

This application is a continuation of PCT/DK93/00183 filed May 26, 1993, which is incorporated herein by reference.

TECHNICAL FIELD

This invention relates to proteases derived from strains of Bacillus sp. More specifically, the invention is directed towards a novel alkaline protease derived from a strain of Bacillus sp. PD498, as well as isolated biologically pure cultures of Bacillus sp. PD498.

Moreover, the invention is directed towards a process for the preparation of the protease, detergent additives and detergent compositions comprising the protease of the invention, and the use of this protease in washing processes.

BACKGROUND ART

Detergent enzymes have been marketed for more than 20 years and are now well established as normal detergent ingredients in both powder and liquid detergents all over the world. With the trend towards lower washing temperature, s detergent enzyme consumption has increased during late years. Enzymes used in washing formulations comprise proteases, lipases, amylases, cellulases, as well as other enzymes, or mixtures hereof. Commercially most important are proteases.

Detergent proteases have been developed by isolation of proteases found in nature followed by testing in detergent formulations. Most detergent of proteases are obtained from members of the genus Bacillus. Currently new types of proteases enter the market, offering the possibility of giving a better cost/performance ratio at various specified conditions.

Examples of commercial protease products are ALCALASE™, ESPERASE™ and SAVINASE™, all supplied by Novo Nordisk A/S, Denmark. These and similar enzyme products from other commercial sources are active in detergent solutions, i.e. at pH values in the range of from 8 to 11 and in the presence of sequestering agents, surfactants and bleaching agents such as sodium borate. The ALCALASE™ protease is produced by strains of the species *Bacillus licheniformis*. The ESPERASE™ and SAVINASE™ proteases are obtained by cultivation of strains of alkalophilic Bacilli.

SUMMARY OF THE INVENTION

According to the present invention novel detergent proteases are provided.

In its first aspect, the invention provides a protease having an apparent molecular weight of 34 kD as determined by SDS-PAGE, a pI of approximately 9.3, a pH optimum in the range of pH 9–11 determined at 25° C. (with casein as substrate), a temperature optimum in the range of 40°–55° C. determined at pH 9.5 (with casein as substrate), and immunochemical properties identical or partially identical to those of a protease derived from Bacillus sp. PD498, NCIMB No. 40484.

In another aspect, the invention provides a protease having an apparent molecular weight of 34 kD as determined by SDS-PAGE, a pI of approximately 9.3, a pH optimum in the range of pH 9–11 determined at 25° C. (with casein as substrate), a temperature optimum in the range of 40°–55° C. determined at pH 9.5 (with casein as substrate), and being obtainable from a strain of Bacillus sp. PD498, or from another host organism carrying the gene encoding a protease having immunochemical properties identical or partially identical to those of the protease derived from Bacillus sp. PD498.

In a third aspect, the invention provides an isolated biologically pure culture of a strain of Bacillus sp. PD498. In a more specific aspect, a strain of Bacillus sp. PD498, NCIMB No. 40484, or a mutant or a variant thereof, is provided.

In a fourth aspect, the invention provides a process for the preparation of the protease, which process comprises cultivation of a protease producing strain of Bacillus sp. PD498 in a suitable nutrient medium, containing carbon and nitrogen sources and inorganic salts, followed by recovery of the desired enzyme. In a more specific aspect, Bacillus sp. PD498, NCIMB No. 40484, or a mutant or a variant thereof, or another host organism carrying the gene encoding a protease having immunochemical properties identical or partially identical to those of the protease derived from Bacillus sp. PD498, is cultivated.

In a fifth aspect, the use of the enzyme as detergent enzyme is claimed. In more specific aspects, the invention provides detergent additives and detergent compositions comprising the protease of the invention. Ultimately, the invention relates to the use of the enzyme of the invention in washing processes.

BRIEF DESCRIPTION OF DRAWINGS

The present invention is further illustrated by reference to the accompanying drawings, in which.

DETAILED DISCLOSURE OF THE INVENTION

The Microorganism

Figure 1:
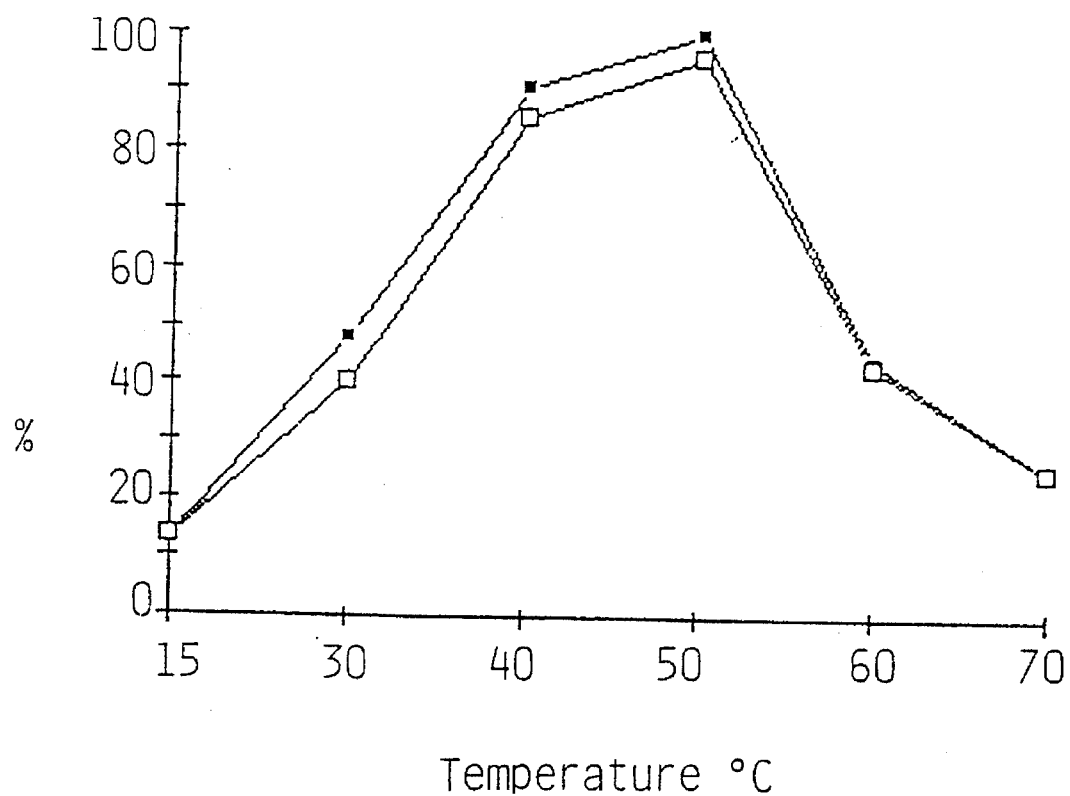
FIG. 1 shows the relation between temperature and the proteolytic activity of an enzyme according to the invention (the enzyme preparation obtained according to Ex. 1, with 2% casein as substrate, determined at pH 9.5; ■ Buffer, □ Buffer+0.1% STPP)

The novel microorganism of the invention, able to produce an enzyme of the invention, was isolated from a soil sample. Bacillus sp. PD498 has been deposited according to the Budapest Treaty at NCIMB, under No. 40484.

The microorganism of this invention is an aerobic, spore forming bacterium belonging to the genus Bacillus. Morphologically it can be described as motile rods with a diameter of 0.7–0.9 micron, and a length of 2–3 micron. The spores are round to ellipsoid, slightly swelling the sporangium, subterminal to terminal. Optimum temperature for growth is within 25°–37° C., and optimal pH for growth is within 7–9, no growth at pH 9.7, and no growth at 50° C. The microorganism forms yellow colonies, round and smooth, on nutrient agar slants, and no diffusion of pigment into the agar is observed.

Cellular Characteristics of PD498

The cellular characteristics of the strain Bacillus sp. PD498 of the invention have been compared to those of the known Bacillus sp. type strains deposited at Deutsche Sammlung von Mikroorganismen und Zellkulturen GmbH, Mascheroder Weg 1B, D-3300 Braunschweig, Germany.

| % Major Fatty Acids: | PD 498 | B. alcalophilus Vedder DSM 2526 | B. alcalophilus subsp. Halodermus DSM 497 |
| --- | --- | --- | --- |
| C 15-1 iso | 30 | 34 | 45 |
| C 15 anteiso | 33 | 32 | 26 |
| C17-1 iso | 2 | 5 | 8 |
| C 17 anteiso | 12 | 12 | 10 |
| Total unsaturated | 6 | 9 | 0 |
| Total unbranched | 4 | 4 | 4 |
| DNA-composition: | | | |
| mol % G + C | 48.8 | 36.2 | 44.1 |

The high G+C percentage in the DNA of PD198 of the invention is a major difference from all other alcaliphilic Bacillus strains studied.

Cultivation of the Microorganism

The microorganism of the invention can be cultivated under aerobic conditions in a nutrient medium containing assimilable carbon and nitrogen together with other essential nutrients, the medium being composed in accordance with the principles of the known art.

Suitable carbon sources are carbohydrates such as sucrose, glucose and starch, or carbohydrate containing materials such as cereal grain, malt, rice and sorghum. The carbohydrate concentration incorporated in the medium may vary widely, e.g. up to 25% and down to 1–5%, but usually 8–10% will be suitable, the percentages being calculated as equivalents of glucose.

The nitrogen source in the nutrient medium may be of inorganic and/or organic nature. Suitable inorganic nitrogen sources are nitrates and ammonium salts. Among the organic nitrogen sources quite a number are used regularly in fermentation processes involving the cultivation of bacteria. Illustrative examples are soybean meal, cotton seed meal, peanut meal, casein, corn, corn steep liquor, yeast extract, urea, and albumin. In addition, the nutrient medium should also contain usual trace substances.

The novel Bacillus species of this invention is slightly alkalophilic. Therefore, the cultivation is preferably conducted at slightly alkaline pH values, which can be obtained by addition of suitable buffers such as sodium bicarbonate, pH 9.0, after sterilization of the growth medium. For cultivation in tank fermentors it is necessary to use artificial aeration. The rate of aeration is similar to that used in conventional tank fermentation.

After fermentation, liquid enzyme concentrates may be produced by removal of coarse material from the broth and, if desired, concentration of the broth by evaporation at low temperature or by ultrafiltration. Finally, preservatives may be added to the concentrate.

Solid enzyme preparations may be prepared from the purified and/or concentrated broth by precipitation with salts, such as $Na_2SO_4$ or water-miscible solvents, such as ethanol or acetone. Removal of the water in the broth by suitable drying methods, such as spray-drying, may also be employed.

Assay for Proteolytic Activity

The proteolytic activity is determined with casein as substrate. One Casein Protease Unit (CPU) is defined as the amount of enzyme liberating 1 mM of primary amino groups (determined by comparison with a serine standard) per minute under standard conditions, i.e. incubation for 30 minutes at 25° C. and pH 9.5. A folder AF 228, describing the analytical method, is available upon request to Novo Nordisk A/S, Denmark, which folder is hereby included by reference.

The Enzyme

The enzyme of the invention is a novel detergent protease. It is an alkaline protease, obtainable by cultivation of a microorganism of the invention, preferably Bacillus sp. PD498, NCIMB No. 40484, or a mutant or a variant thereof, in a suitable nutrient medium, containing carbon and nitrogen sources and inorganic salts. The enzyme can also be obtained by recombinant DNA-technology.

The protease of the invention can be described by the following characteristics.

Physical-Chemical Properties.

The protease of the invention has an apparent molecular weight of 34 kD when determined by SDS-PAGE. A pI of approximately 9.3 was determined by isoelectric focusing on LKB Ampholine®PAG plates. The protease activity is inhibited is by PMSF, a serine proteinase inhibitor. EDTA and soybean-protein inhibitor do not influence the protease activity.

The temperature activity relationship is presented on FIG. 1. The activity was determined with 2% casein as substrate at pH 9.5 in the presence (white squares) and absence (black squares) of 0.1% sodium tripolyphosphate (STPP, a common ingredient in many commercial detergents). The assay for proteolytic activity described previously was used with the modification that the incubation temperature was varied in the interval of from 15° to 70° C. It appears from the figure that the enzyme possesses proteolytic activity from 15° C. to 70° C., and has a temperature optimum in the range of from 40°–55° C., around 50° C.

Figure 2:
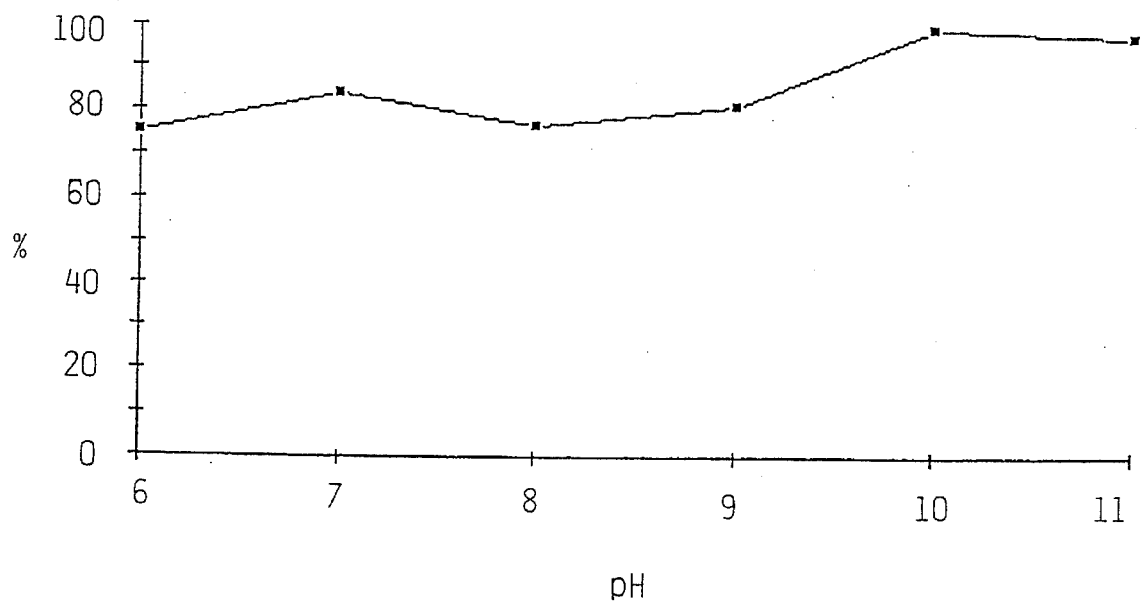
FIG. 2 shows the relation between pH and the proteolytic activity of an enzyme according to the invention (the enzyme preparation obtained according to Ex. 1, with 1% casein as substrate, determined at 25° C.)

The dependence of activity on pH was determined by the same procedure, using buffers adjusted to predetermined pH values in the pH range of from 6 to 11. The result is shown in FIG. 2. It appears from this figure that the enzyme possesses proteolytic activity in a very broad pH range of from below pH 6 to above pH 11, with an apparent pH optimum in the range of from pH 9–11, around pH 10.

Furthermore, it was found that the protease of the invention is stable for 60 minutes at 25° C. under washing conditions when determined in European type and American type detergents.

Immunochemical Properties

The protease of the invention has immunochemical properties identical or partially identical (i.e. at least partially identical) to those of a protease derived from the strain Bacillus sp. PD498, NCIMB No. 40484.

The immunochemical properties can be determined immunologically by cross-reaction identity tests. The identity tests can be performed by the well-known Ouchterlony double immunodiffusion procedure or by tandem crossed immunoelectrophoresis according to N.H. Axelsen; Handbook of Immuno-precipitation-in-Gel Techniques; Blackwell Scientific Publications (1983), chapters 5 and 14. The terms "antigenic identity" and "partial antigenic identity" are described in the same book, Chapters 5, 19 and 20.

Monospecific antiserum was generated according to the above mentioned method by immunizing rabbits with the purified protease of the invention. The immunogen was mixed with Freund's adjuvant and injected subcutaneously into rabbits every second week. Antiserum was obtained after a total immunization period of 8 weeks, and immunoglobulin was prepared therefrom as described by N.H. Axelsen, supra.

Ouchterlony double immunodiffusion tests showed no cross reaction between the protease of the invention and the known alkaline serine proteases from Bacillus species, e.g. ALCALASE™, SAVINASE™, ESPERASE™, subtilisin Novo (available from Novo Nordisk A/S, Denmark), and KAZUSASE™ (available from SHOWA DENKO, Japan).

Detergent Compositions

The detergent composition of the invention may comprise one or more surfactants, which may be of an anionic, non-ionic, cat-ionic, amphoteric or zwitter-ionic type, or a mixture of these. Typical examples of anionic surfactants are linear alkyl benzene sulfonates (LAS), alkyl sulfates (AS), alpha olefin sulfonates (AOS), alcohol ethoxy sulfates (AES) and alkali metal salts of natural fatty acids. Examples of non-ionic surfactants are alkyl polyethylene glycol ethers, nonylphenol polyethylene glycol ethers, fatty acids esters of sucrose and glucose, and esters of polyethoxylated alkyl glucoside.

The detergent composition of the invention may also contain other detergent ingredients known in the art such as builders, bleaching agents, bleach activators, anti-corrosion agents, sequestering agents, anti soil-redeposition agents, perfumes, stabilizers for the enzymes and bleaching agents, formulations aids, optical brighteners, foam boosters, chelating agents, fillers, fabric softeners, etc. The detergent composition of the invention may be formulated substantially as described in Falbe, J. [Falbe, J.; Surfactants in Consumer Products. Theory, Technology and Application; Springer Verlag 1987, vide in particular the section entitled "Frame formulations for liquid/powder heavy-duty detergents"].

It is at present contemplated that the detergent composition of the invention may contain the enzyme preparation in an amount corresponding to 0.0005–0.5 CPU of the proteolytic enzyme per liter of washing liquor.

The detergent compositions of the invention can be formulated in any convenient form, such as powders, liquids, etc.

The detergent composition of the invention may advantageously include one or more other enzymes, e.g. lipases, amylases, cellulases, oxidases, and/or peroxidases, conventionally included in detergent compositions.

The protease of the invention may be included in a detergent composition by adding separate additives containing the detergent protease, or by adding a combined additive comprising different detergent enzymes.

The additive of the invention can be formulated e.g. as granulates, liquids, slurries, etc. Preferred detergent additive formulations are non-dusting granulates, liquids, in particular stabilized liquids, slurries, or protected enzymes. Dust free granulates may be produced e.g. according to GB Patent Publication No. 1,362,365 or U.S. Pat. No. 4,106,991, and may optionally be coated by methods known in the art. The detergent enzymes may be mixed before or after granulation. Liquid enzyme preparations may, for instance, be stabilized by adding a polyol such as e.g. propylene glycol, a sugar or sugar alcohol, lactic acid or boric acid, according to established methods. Other enzyme stabilizers are well known in the art. Protected enzymes may be prepared according to the method disclosed in EP Patent Publication No. 238,216.

The invention is further illustrated in the following examples, which are not intended to be in any way limiting to the scope of the invention as claimed.

EXAMPLE 1

Bacillus sp. PD498 was cultivated at 25° C. on a rotary shaking table (300 r.p.m.) in 500 ml baffled Erlenmeyer flasks containing 100 ml of medium of the following composition (per liter):

| | |
|---|---|
| Potato starch | 100 g |
| Ground barley | 50 g |
| Soybean flour | 20 g |
| $Na_2HPO_4 \times 12\ H_2O$ | 9 g |
| Pluronic ® | 0.1 g |
| Sodium caseinate | 10 g |

The starch in the medium is liquified with α-amylase, and the medium is sterilized by heating at 120° C. for 45 minutes.

After sterilization the pH of the medium is adjusted to 9.0 by addition of 10 ml of a 1 M solution of sodium bicarbonate.

After 4 days of incubation the proteolytic activity of the culture was determined using the method described above.

After cultivation, the enzyme activity of the broth was 5 CPU/l.

After separation of the solid material the protease was purified by a conventional chromatographic method.

Yield from 3.5 l of culture broth was 31 ml with 120 CPU/l. Purity was more than 90% as judged by both SDS-PAGE and isoelectric focusing.

The characteristics of the preparation prepared in accordance with this Example have been referred to earlier in this specification, and reference is made hereto.

EXAMPLE 2

Wash Performance

The wash performance tests were accomplished on grass soiled cotton, at 20° C., isothermally for 10 minutes.

The tests were performed at enzyme concentrations between 0.02 and 0.5 mg of enzyme protein per liter.

2.0 g/l of a commercial US powder detergent were used. The detergent was dissolved in approx. 6° dH (German Hardness) water, and pH was adjusted to 9.5. The textile/wash liquor ratio was 6 g of textile per liter of wash liquor.

Subsequent to washing, the cloths were flushed in running tap water and air-dried. The remission (%R) at 460 nm was determined.

As a measure of the wash performance differential remission, ΔR, was used being equal to the remission after wash with enzyme added, minus the remission after wash with no enzyme added.

Figure 3:
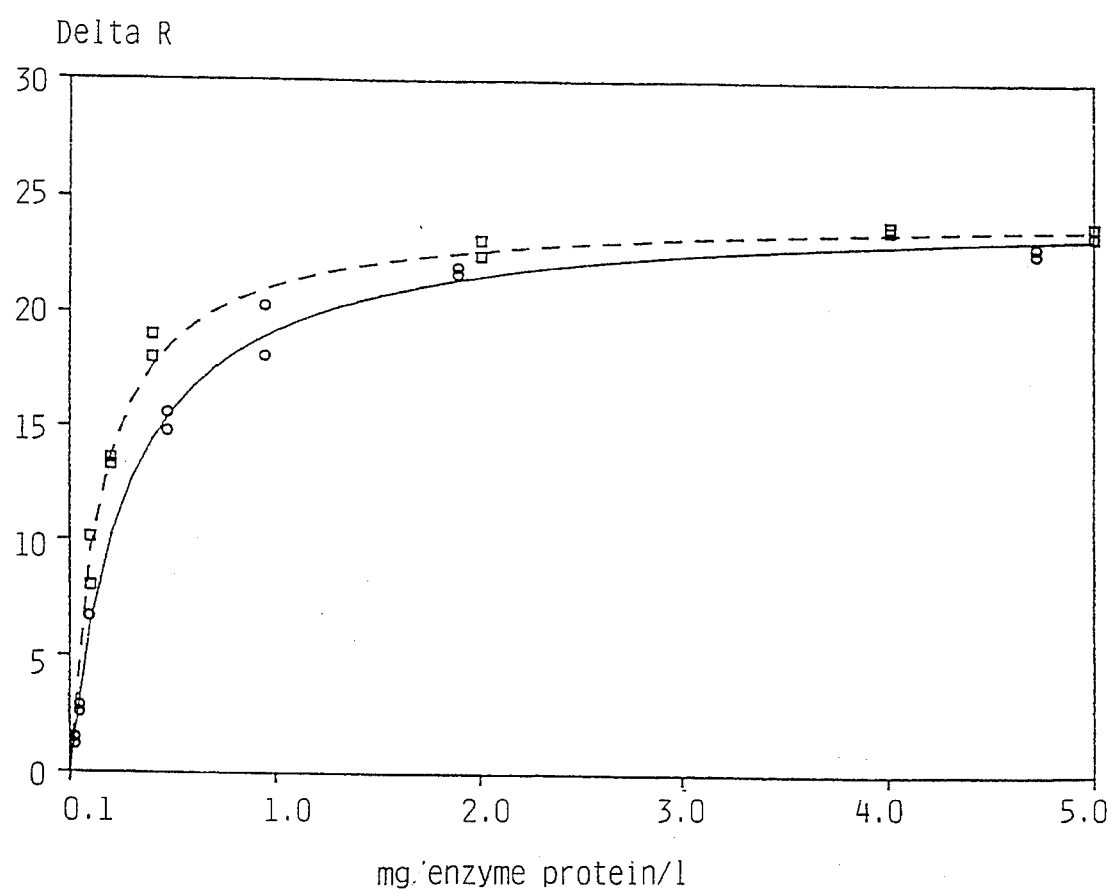
FIG. 3 shows the washing performance of an enzyme of the invention compared to a commercial detergent enzyme (□ the enzyme preparation obtained according to Ex. 1; ○ Savinase™, Novo Nordisk A/S, Denmark).

The results of these tests are shown in FIG. 3. It appears from the figure that the protease of the invention possesses good washability.

We claim:

1. An isolated protease obtainable from Bacillus sp. PD498, NCIMB No. 40484 having the following properties:
   a. an apparent molecular weight of 34 kD as determined by SDS-PAGE;
   b. pI of approximately 9.3;

c. pH optimum of pH 9–11 at 25° C. and with casein as substrate; and d. temperature optimum of 40°–55° C. at pH 9.5 and with casein as substrate.

2. The isolated protease of claim 1, in which the protease is obtained from the strain Bacillus sp. PD498, NCIMB No. 40484.

3. A process for the preparation of the protease according to claim 1, which process comprises cultivating a strain of Bacillus capable of producing said protease in a nutrient medium containing carbon and nitrogen sources and inorganic salts, followed by recovery of said protease.

4. The process according to claim 3, in which the strain is Bacillus sp. PD498, NCIMB No. 40484.

5. A detergent additive comprising the protease according to claim 1 provided in the form of a non-dusting granulate, a liquid, or a slurry.

6. A detergent additive comprising the protease according to claim 1 provided in a protected enzyme form.

7. The detergent additive according to claim 5 provided in the form of a liquid or a slurry.

8. A detergent composition comprising the protease according to claim 1.

9. The detergent composition according to claim 8, which further comprises at least one other enzyme.

10. The detergent composition according to claim 9 in which the at least one other enzyme is selected from the group consisting of amylases, lipases, cellulases, and oxidases.

11. The detergent composition according to claim 10, wherein the oxidase is a peroxidase.

12. A process of washing comprising adding the protease according to claim 1 during washing.

13. A process of washing comprising adding the detergent additive according to any of claims 5–7 during washing.

14. A process of washing comprising adding the detergent composition according to any of claims 8–11 during washing.

* * * * *